United States Patent [19]

Spicer et al.

[11] 4,018,932
[45] Apr. 19, 1977

[54] ANTHELMINTIC POUR-ON FORMULATIONS FOR TOPICAL USE ON DOMESTIC AND FARM ANIMALS

[75] Inventors: Larry Dean Spicer, Princeton; James Michael Quinlan, Trenton; Harold Berger, Lawrenceville, all of N.J.

[73] Assignee: American Cyanamid Company, Stamford, Conn.

[22] Filed: Nov. 3, 1975

[21] Appl. No.: 628,458

[52] U.S. Cl. ............................................. 424/270
[51] Int. Cl.² ...................................... A61K 31/425
[58] Field of Search ................................. 424/270

[56] References Cited
FOREIGN PATENTS OR APPLICATIONS
773,062   3/1972   Belgium OTHER PUBLICATIONS
Shulz et al., Chem. Abst. vol. 82 (1975), p. 160248h.

Primary Examiner—Sam Rosen
Attorney, Agent, or Firm—Harry H. Kline

[57] ABSTRACT

There is provided a method for the control of helminths infecting homothermic domestic and farm animals wherein there is introduced into said animals' circulatory system an anthelmintically effective amount of a racemic mixture of either a substituted 6-(m-aminophenyl)-2,3,5,6-tetrahydro-imidazo[2,1-b]thiazole or an optically active levorotatory (1) isomer thereof by percutaneous absorption.

13 Claims, No Drawings

ANTHELMINTIC POUR-ON FORMULATIONS FOR TOPICAL USE ON DOMESTIC AND FARM ANIMALS

Helminth infections of homothermic domestic and farm animals are the cause of significant economical losses in animal agriculture. Efficient control of these pests is highly desirable and can be achieved by introducing into said animals circulatory system an anthelmintically effective amount of a compound of the formula:

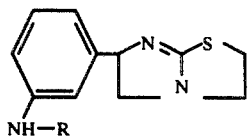

wherein R is hydrogen, lower alkanoyl or the radical:

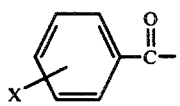

where X is either hydrogen or halogen; and said compound may comprise a racemic (dl) mixture or levorotatory optical isomers thereof. The compounds are prepared by the process described in Belgium Pat. No. 773,062.

This control is accomplished by the percutaneous absorption and/or penetration from a liquid formulation when applied directly to said animals' skin. It is a preferred practice to employ a compound represented by the above formula wherein R is isobutyryl, pivaloyl, benzoyl, or m and p-chlorobenzyl, said compounds are the racemic (dl) mixtures or the optical isomers thereof.

Pharmaceutically acceptable salts of the hereinabove defined formula compounds are suitable for the preparation of liquid formulation hereinafter referred-to as pour-ons. Such formulations are applied to the skin of domestic or farm animals.

The above referred-to salts of the compounds above defined can be prepared by reacting said compound with a stochiometric or slight excess from 10% to 20% of an organic or inorganic acid selected from the group consisting of hydrochloric acid, sulfuric acid, phosphoric acid, a $C_5$-$C_{18}$ straight chain or branched alkanoic acid, a $C_3$-$C_9$ dicarboxylic acid, a half ester of a $C_3$-$C_9$ dicarboxylic acid, nicotinic acid and the like.

A number of delivery systems have been devised and are available for the administration of drugs to homothermic domestic and farm animals. For instance feed premixes and concentrates can be added to or sprinkled on a nutritionally balanced animal diet, pills, boluses, oral drenches, injectables and the like. However, though effective, the above modes of administration of drugs to said animals are time consuming and expensive especially if a large number of animals are to be treated. Moreover, with some modes of delivery, e.g. with the injectables, side reactions such as swelling, erythema and tissue necrosis at the site of the injection are not uncommon occurrences.

In contrast, pour-on formulations are easy to apply, a large number of animals can be dosed rapidly and in addition such formulations are usually free from undesirable side effects as hereinabove described. Advantageously the active compounds rapidly enter the animals circulatory system by percutaneous absorption.

As hereinabove stated formula (I) anthelmintic compounds are eminently suitable for the control of helminths infecting farm animals such as cattle, sheep, horses, and the like, when introduced into said animals circulatory system by percutaneous absorption and/or penetration from a pour-on formulation applied topically to said animals skin in amounts sufficient to supply 1 mg to 30 mg per kg animal body weight and preferably 1 mg to 10 mg per kg animal body weight of active compound.

Pour-on formulation may also offer an additional advantage, not realized by other modes of delivery, namely that the active compound contained therein is absorbed by the skin, creating a temporary reservoir of active compound within the skin from which the active compound is released more or less at a steady rate into said animals circulatory system and thus a relatively even level of concentration of active compound is maintained in the blood until the drug supply is exhausted.

To prepare a pour-on formulation, the compound or an acid addition salt thereof as hereinabove defined is dissolved in a suitable solvent. Exemplary of the latter are: an aromatic hydrocarbon such as toluene or xylene, a lower dialkylphthalate, a polypropylene glycol, such as dipropylene glycol or tripropylene glycol, an ethylene or propylene carbonate, a dialkyl sulfoxide such as dimethyl-, methyl octyl- or methyl decyl sulfoxide, a lower alkyl ester of an alkanoic acid, an alkyl ester of levulinic or salicylic acid, as lower aliphatic alcohol such as methanol, ethanol, propanol or butanol, a lower cyclic aliphatic ketone, a $C_4$-$C_8$ aliphatic ketone, glycerol formal, dioxolane, N,N-dimethyl- or diethyl nicotinamide, a thioacetic ester such as a lower alkyl thioglycolate, a $C_7$-$C_{12}$ aliphatic and cyclic hydrocarbon, an aliphatic or aromatic aldehyde, a lower alkyl- or aromatic ester of an aromatic acid or mixtures thereof.

The pour-on formulations of this invention can contain the hereinabove-defined compound in the range of 0.5% wt/vol to 40% wt/vol and, preferably, 1% wt/vol to 10% wt/vol. Emollients, such as mineral oils, corn oil, peanut oil, olive oil, tallow, lanolin, polyethylene glycol and equivalents thereof can be added to the above pour-on formulations in amounts from 1% vol/vol to 20% vol/vol and, preferably, 5% vol/vol to 10% vol/vol, if desired to minimize possible local irritations or drying of the animals skin due to the solvent of said formulation.

Additionally, any commercially available surfactant may also be incorporated into the above pour-on formulations containing an anthelmintic compound, above-defined, to decrease the surface tension of said formulations and thus promote wetting of the animal's skin with said formulation. The surfactants can be added in amounts from 0.1% wt/vol to 10% wt/vol and preferably 0.2% wt/vol to 2.0% wt/vol of pour-on formulation. Illustrative and suitable surfactants contemplate the condensates of ethylene oxide with fatty acids and fatty alcohol, octylphenol and the like, sodium salts of fatty acids, sodium salts of sulfonates such as sodium dodecylsulfonate, sodium alkylbenzene sulfonates and the like, condensation products of fatty acids with N-methyltaurine and equivalents thereof.

The following non-limiting examples are given to further illustrate the invention of the present application.

EXAMPLE 1

Preparation of a Pour-on Solution Containing dl-6-(m-benzoylaminophenyl)-2,3,5,6-tetrahydroimidazo[2,1-b]thiazole hydrochloride The hereinabove compound (0.34 g) and deionized water (2.0 ml) are mixed in a suitable reaction vessel, and dimethyl sulfoxide added to adjust the volume of the solution to 20.0 ml. The resulting clear solution contains 1.6% wt/vol of dl-6-(m-benzoylaminophenyl)-2,3,5,6-tetrahydroimidazo[2,1-b]thiazole hydrochloride.

Similarly, a pour-on solution is prepared, containing 1.6% wt/vol of dl-6-[m-(-chlorobenzoyl)aminophenyl]-2,3,5,6tetrahydroimidazo[2,1-b]thiazole hydrochloride when substituting the latter for the benzoylaminophenyl derivative employed.

EXAMPLE 2

Preparation of a Pour-on Solutions Containing 1-and dl-6-(m-isobutyrylaminophenyl)-2,3,5,6-tetrahydroimidazo[2,1-b]-thiazole hydrochloride, respectively The above-noted compounds (0.34 g) are separately dissolved in dimethyl sulfoxide (8.0 ml) and cyclohexanone added to adjust the volume of the solutions to 20.0 ml. The resulting clear solutions contain 1.6% wt/vol of 1-and dl-6-(m-isobutyrylaminophenyl)-2,3,5,6-tetrahydroimidazo[2,1-b]thiazole hydrochloride, respectively.

Similarly, pour-on solutions are prepared, containing 1.6% wt/vol of the 1-and dl-6-(m-pivaloylaminophenyl)-2,3,5,6-tetrahydroimidazo[2,1-b]thiazole hydrochloride.

EXAMPLE 3

Preparation of a Pour-on Solution Containing 1-and dl-6-(m-isobutyrylaminophenyl)-2,3,5,6-tetrahydroimidazo[2,1-b]-thiazole base, respectively The above-identified compounds (0.30 g) are separately dissolved in cyclohexanone. Xylene (5.6 ml) and corn oil (2.0 ml) are added and the volume of the solutions are adjusted to 20.0 ml with cyclohexanone. The resulting clear solutions contain 1.42% wt/vol of 1-and dl-6-(m-isobutyrylaminophenyl)-2,3,5,6-tetrahydroimidazo[2,1-b]thiazole base, respectively.

Similarly, a pour-on solution is prepared, containing 1.42% wt/vol of dl-6-(m-pivaloylaminophenyl)-2,3,5,6-tetrahydroimidazo[2,1-b]thiazole base.

EXAMPLE 4

Preparation of a Pour-on Solution Containing dl-6-(m-isobutyrylaminophenyl)-2,3,5,6-tetrahydroimidazo[2,1-b]thiazole base The above-noted compound (0.30 g) is dissolved in isopropanol, mineral oil (2.0 ml) is added and the volume of the solution adjusted to 20.0 ml with isopropanol. The resulting clear solution contains 1.42% wt/vol of dl-6-(m-isobutyrylaminophenyl)-2,3,5,6-tetrahydroimidazo[2,1-b]-thiazole.

EXAMPLE 5

Example 4 is repeated in every respect except that isoamyl alcohol is substituted for the isopropyl alcohol.

EXAMPLE 6

Preparation of a Pour-on Solution Containing dl-6-(m-benzoylaminophenyl)-2,3,5,6-tetrahydroimidazo[2,1-b]thiazole base The above-noted compound (0.30 g) is dissolved in cyclohexanone (13.0 ml) and the volume of the solution adjusted to 20.0 ml with xylene. The resulting clear solution contains 1.44% wt/vol of dl-6-(m-benzoylaminophenyl)-2,3,5,6-tetrahydroimidazo[2,1-b]thiazole base.

Similarly, a pour-on solution is prepared, containing 1.44% wt/vol of dl-6-[m-(3-chlorobenzoyl)aminophenyl]-2,3,5,6-tetrahydroimidazo[2,1-b]thiazole base.

EXAMPLE 7

Preparation of a Pour-on Solution Containing dl-6-(m-benzoyl)aminophenyl[2,3,5,6-tetrahydroimidazo[2,1-b]thiazole base The above-noted compound (0.30 g) is dissolved in isopropanol, mineral oil (2.0 ml) added and the volume of the solution is adjusted to 20.0 ml with isopropanol. The resulting clear solution contains 1.44% wt/vol of dl-6-(m-benzoylaminophenyl)-2,3,5,6-tetrahydroimidazo[2,1-b]thiazole base.

EXAMPLE 8

Example 7 is repeated except isoamyl alcohol is substituted for isopropyl alcohol.

EXAMPLE 9

Preparation of a Pour-on Solution Containing Methyl 5-(phenylthio)-2-benzimidazole Carbamate The above-identified compound (0.42 g) is dissolved in dimethyl sulfoxide (8.0 ml) and the volume of the solution adjusted to 20.0 ml with cyclohexanone. The resulting clear solution contains 2% wt/vol of methyl 5-(phenylthio)-2-benzimidazole carbamate.

EXAMPLE 10

Thirty New Zealand white rabbits 6 – 8 weeks of age are experimentally infected with 2000 to 2500 *Trichostrongylus colubriformis* larvae by means of a No. 6 French rubber catheter attached to a syringe containing the inoculum while being temporarily anesthetized with Nembutal. Twenty-three days after inoculation a pretreatment fecal egg count is made to determine the uniformity of infection in the test. The rabbits are then allotted to 10 groups of 3 animals each, based on pretreatment fecal egg count.

Each of the experimental pour-on formulation is applied at the rate of 0.5 ml per kg body weight corresponding to 8 mg per kg body weight of the compound above-identified expressed as the hydrochloride thereof and 10 mg per kg body weight for methyl 5-(phenylthio)-2-benzimidazole carbamate, a commercially available anthelmintic included for comparison. One group of rabbits serves as infected untreated control.

An area of approximately 1×3 inches is shaved along the back of each animal for site of pour-on application.

A circular collar 7" in diameter is placed around the neck of each rabbit to prevent ingestion of the drug under test by grooming. Three days after treatment the rabbits are necropsied and worm counts made. Percent efficacy is calculated using the formula:

$$\% \text{ Efficacy} = \frac{\text{No. of worms found in controls} - \text{No. of worms found in treated animals}}{\text{No. of worms found in controls}} \times 100$$

The data obtained are given in Table I below:

Table I

| Percent Efficacy of Substituted 6-(m-aminophenyl)-2,3,5,6-tetrahydroimidazo[2,1-b]thiazole compounds against *Trichostrongylus colubriformis* in the Rabbit | | |
|---|---|---|
| Example | Average Amount of Formulation Applied in cc | No. of Worms Recovered at Necropsy | Efficacy in % |
| 1 | 1.03 | 49 | 61 |
| 2 | 1.10 | 3 | 98 |
| 3 | 1.10 | 37 | 70 |
| 4 | 1.02 | 27 | 78 |
| 5 | 1.05 | 198 | 0 |
| 6 | 1.17 | 52 | 58 |
| 7 | 1.11 | 54 | 57 |
| 8 | 1.16 | 178 | 0 |
| 9 | 1.11 | 170 | 0 |
| Control | — | 124 | — |

We claim:
1. A method for the control of helminths infecting homothermic domestic and farm animals comprising, directly contacting the skin of said animals with a solution containing an anthelmintically effective amount of (a) a compound of the formula:

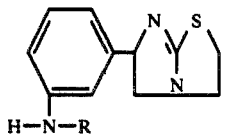

wherein R is selected from the group consisting of lower alkanoyl and

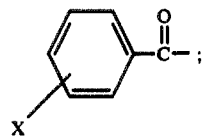

X is selected from the group consisting of hydrogen and halogen, or (b) the racemic (dl) mixtures or (c) an optically active levorotatory isomer thereof; and wherein said compound is the free base or an acid addition salt thereof.

2. The method according to claim 1, wherein R is selected from the group consisting of isobutyryl, pivaloyl, benzoyl, m-chlorobenzoyl and p-chlorobenzoyl.

3. The method according to claim 1, wherein said compound is 6-(m-isobutyrylaminopenyl)-2,3,5,6-tetrahydroimidazo[2,1-b]thiazole.

4. The method according to claim 1, wherein said compound is 6-(m-benzoylaminophenyl)-2,3,5,6-tetrahydroimidazo[2,1-b]thiazole.

5. The method according to claim 1, wherein said compound is as defined in claim 1, and said solution is administered to the skin of said animals in amounts sufficient to deliver from about 1 mg to about 30 mg per kg animal body weight of active compound.

6. The method according to claim 5 wherein said compound is administered in amounts from about 1 mg to about 10 mg per kg animal body weight.

7. The method according to claim 1 wherein said animals are cattle, sheep or horses.

8. An anthelmintic pour-on solution comprising: (1) from about 0.5% to about 40% by weight per volume of a solution of (a) a compound of the formula:

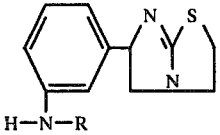

wherein R is selected the group consisting of from lower alkanoyl and

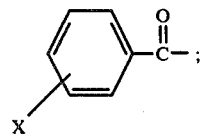

X is selected from the group consisting of hydrogen and halogen,
b. the racemic (dl) mixtures, thereof, or
c. an optically active levorotatory isomer thereof; and wherein said compound is the free base or an acid addition salt thereof; and (2) the balance being a solvent selected from the group consisting of a $C_1$-$C_4$ aliphatic alcohol, a $C_4$-$C_8$ aliphatic ketone, a $C_5$-$C_7$ aliphatic cyclic ketone, a $C_1$-$C_4$ alkyl ester of $C_5$-$C_{10}$ alkanoic acid, a $C_1$-$C_4$ alkyl ester of levulinic acid, a $C_1$-$C_4$ alkyl ester of salicylic acid, N,N-dimethyl nicotinamide, N,N-diethyl nicotinamide, a $C_1$-$C_4$ dialkyl phthalate, dimethyl sulfoxide, methyl octyl sulfoxide, methyl decyl sulfoxide, a $C_7$-$C_{12}$ aliphatic or cyclic hydrocarbon, a $C_7$-$C_8$ aromatic hydrocarbon, mineral oils, corn oil, peanut oil, olive oil, dipropylene glycol, tripropylene glycol, or mixtures thereof.

9. An anthelmintic solution according to claim 8, wherein said compound is present in an amount ranging from about 1% to about 10%, by weight, per volume of solution.

10. An anthelmintic solution according to claim 8, wherein said compound is 6-(m-isobutyrylaminophenyl)-2,3,5,6-tetrahydroimidazo[2,1-b]thiazole.

11. An anthelmintic solution according to claim 8, wherein said compound is 6-(m-benzoylaminophenyl)-2,3,5,6-tetrahydroimidazo[2,1-b]thiazole.

12. An anthelmintic solution according to claim 8, wherein said compound is 6-(m-pivaloylaminophenyl)-2,3,5,6-tetrahydroimidazo[2,1-b]thiazole.

13. An anthelmintic solution according to claim 8, wherein said compound is 6-[m-(4-chlorobenzoyl)-aminophenyl]-2,3,5,6-tetrahydroimidazo[2,1-b]thiazole.

* * * * *